United States Patent [19]

Briet et al.

[11] 4,097,582
[45] Jun. 27, 1978

[54] 6',2-(2'-ARYLCHROMONYL) PROPIONIC ACIDS, AND ANALGESIC AND ANTI-INFLAMMATORY DERIVATIVES THEREOF

[75] Inventors: Philippe Briet; Jean-Jacques Berthelon; Jean-Claude Depin, all of Lyon; Eugéne Boschetti, Venissieux, all of France

[73] Assignee: Lipha, Lyonnaise Industrielle Pharmaceutique, Lyon, France

[21] Appl. No.: 631,401

[22] Filed: Nov. 12, 1975

[30] Foreign Application Priority Data

Nov. 20, 1974 France .............................. 74 38080
Oct. 10, 1974 France .............................. 75 31024

[51] Int. Cl.$^2$ ................... A61K 31/35; C07D 311/02; C07D 295/00
[52] U.S. Cl. .............. 424/283; 260/332.2 A; 260/345.2; 424/248.4; 424/248.51; 424/248.53; 424/248.55; 424/275; 544/146; 544/151
[58] Field of Search ............. 260/345.2; 424/283; 544/151

[56] References Cited

FOREIGN PATENT DOCUMENTS 2,511,647 9/1975 Germany .................. 260/345.2

OTHER PUBLICATIONS

Patel et al., J. Indian Chem. Soc., 50, 295 (1973).

Primary Examiner—Nicky Chan
Attorney, Agent, or Firm—Browdy and Neimark

[57] ABSTRACT

Propionic acids and their functional derivatives having anti-inflammatory and analgesic properties correspond to the formula

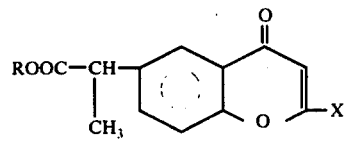

in which X is selected from phenyl, halophenyl, polyhalophenyl, lower alkylphenyl, trihalomethylphenyl, aryloxyphenyl, furyl and thienyl and R is selected from hydrogen, lower alkyl, lower omega-hydroxyalkyl, morpholinoethyl and lower dialkylaminoalkyl.

10 Claims, No Drawings

6',2-(2'-ARYLCHROMONYL) PROPIONIC ACIDS, AND ANALGESIC AND ANTI-INFLAMMATORY DERIVATIVES THEREOF

This invention relates to new carboxylic acids which are substituted by a chromonyl group, and more particularly to substituted propionic acids, to functional derivatives thereof, more especially their esters, and to intermediate products used in their preparation, to the methods of preparing them, and to their use.

6-(2-Phenylchromonyl) acetic acid is known. The chemical compound was described by S. Patel and S. Sethna (Journal of the Indian Chemical Society, 1973, Volume 50 pages 295–8) its choleretic activity has been recently discovered.

New compounds have now been discovered which have remarkable analgesic and anti-inflammatory properties which are only slightly ulcerating.

The propionic acids and their derivatives of the present invention are represented by the general formula:

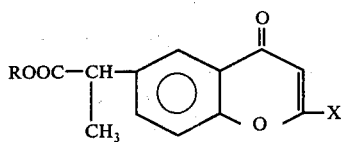

in which X is a phenyl group, a substituted phenyl group, a furyl group or a thienyl group, the substituents in the phenyl group being at least one halogen, preferably chlorine a lower alkyl group, preferably methyl, trihalomethyl or aryloxy; and R is hydrogen, a lower alkyl group, a lower dialkylaminoalkyl group, a lower ω-hydroxyalkyl group, or a morpholinoethyl group.

The addition salts which the basic functional derivatives form with pharmaceutically acceptable acids and the salts with mineral and organic bases of the acids themselves also constitute a feature of this invention.

The propionic acids may be prepared from the methyl esters of the corresponding acetic acids; The methyl ester of a corresponding acetic acid is converted into the corresponding ethyl malonate by treatment with ethyl carbonate and sodium hydride. When the interesterification reaction is complete the alkaline medium enables the carbanion to be obtained, which is then alkylated with methyl iodide in dimethylformamide.

Treatment of the alkylation product with a mixture of acetic acid and hydrochloric acid enables the two ester functions to be hydrolysed and the liberated malonic acid undergoes decarboxylation. The reaction proceeds as follows

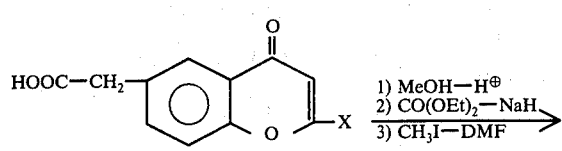

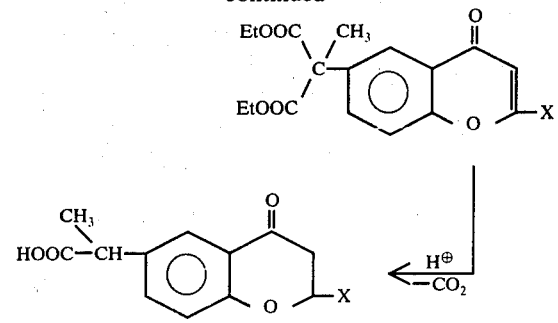

The acetic acids which constitute the starting materials form a part of the invention and have the general formula:

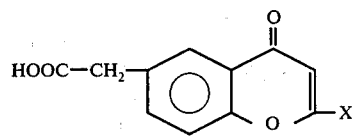

in which X is as defined above (except when X is a phenyl group). They may be obtaibed by either of two different routes viz. from 5-methyl-2-hydroxyacetophenone or from o-hydroxyacetophenone respectively. Each method comprises five stages, three of which are common to both methods.

METHOD A

5-Methyl-2-hydroxyacetophenone is condensed with an ethyl carboxylate of the group X dissolved in a dry aromatic solvent in the presence of sodium hydride. The dibenzoyl methane thus obtained is cyclised to the corresponding chromone by treatment with acid.

The 5-methyl group of the original acetophenone is then converted into the corresponding carboxymethyl group by bromination using N-bromosuccinimide (NBS), followed by treatment with an alkali metal cyanide, and then hydrolysing with acid,

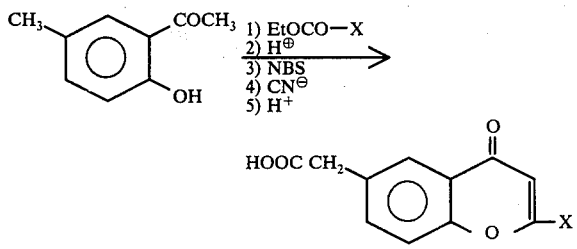

METHOD B

5-Methoxymethyl-2-hydroxyacetophenone prepared from the corresponding chloromethyl compound is condensed with an ethyl carboxylate of the group X in the presence of sodium hydride in a dry aromatic solvent or in dimethyl sulphoxide. The dibenzoylmethane thus obtained is then cyclised with hydrobromic acid to give the corresponding bromomethylchromone, which latter is then treated with an alkali cyanide and then hydrolysed with acid.

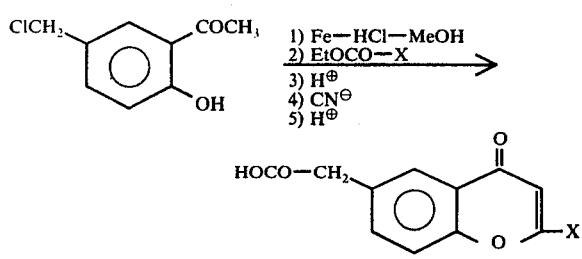

In the three reaction diagrams above, X is as previously defined.

The preparation of the esters of the propionic acids may be carried out employing known methods, more especially by the action of an alcohol ROH (R being a lower alkyl group, a lower ω-hydroxylalkyl group, a lower dialkylaminoalkyl group or a morpholinoethyl group) upon the corresponding acid, or that of an alkyl halide upon the sodium or potassium salt of the acid.

The pharmacological, analgesic and anti-inflammatory effectiveness and the slightly ulcerating effect of the propionic acids and their functional derivatives was determined by various methods. The compounds are identified by the numbers of the examples.

The analgesic effect of the compounds of the invention was shown by means of the acetic test upon mice (the method of Siegmund as modified by Koster, Anderson and Debeer).

In the appended Table I the effective doses $ED_{50}$ in mg/kg determined upon some of the compounds tested are given (aspirin was used as a control).

Table I

| Substance  | $ED_{50}$ in mg/kg |
|------------|--------------------|
| Aspirin    | 130                |
| Example 13 | 1.5                |
| Example 22 | 9                  |
| Example 25 | 6                  |
| Example 29 | 2.3                |
| Example 32 | 4.6                |

The anti-inflammatory effect of the compounds claimed was established, inter alia, by the carrageenin-induced oedema test upon rats (Winter et al. — Proc. Soc. Exp. Biol. Med. 1962, Vol. III, pages 544 and 547). The results obtained with certain of the compounds of the invention are given below in Table II (phenylbutazone was used as a control).

Table II

| Substance      | Carrageenin (A.D. 30, mg/kg) |
|----------------|------------------------------|
| Phenylbutazone | 50                           |
| Example 13     | 10                           |
| Example 22     | 65                           |
| Example 25     | 85                           |
| Example 29     | 37                           |

The compounds were compared with phenylbutazone in order to evaluate their ulcerating effect. The method used was that of aggravating ulcers which has already been caused in rats by the procedure described by Shay et al (Gastroenterology, 1945, Vol. 5, pages 43 to 61). Table III gives the results obtained using two preferred compounds of the present invention and demonstrates the advantageous character of these compounds.

Table III

| | Aggravation of ulceration | |
|---|---|---|
| Substance | Dose: mg/kg body weight/PO | Coefficient |
| Phenylbutazone | 200 | 100 |
| Example 22 | 300 | 60 |
| Example 13 | 300 | 50 |

Pharmaceutical compositions containing a compound of the invention as their active ingredient, either in the form of a base or in the form of the corresponding organic or mineral salt, may be in the form of tablets, pills, capsules, lozenges, aqueous suspensions, injectable solutions, sprays, syrups and the like.

The tablets may, if desired, be made resistant to attack by gastric juices by coating them with a cellulose derivative.

Pharmaceutical compositions comprising a compound of the invention as their active ingredient and a physiologically acceptable, solid or liquid pharmaceutical excipient or diluent enable the active ingredient to be administered in daily doses of from 20 to 1000 mg. Among the observations made during clinical trials with the compound of Example 13 the following may be mentioned:

Observation 1

Mrs. G — 60 years old — Post-fracture gonarthrosis of the left knee.

Treatment with the active ingredient of Example 13 in doses of four 100 mg tablets per day for 10 days gave excellent results on the knee, which returned to its normal temperature and whose flexion improved from 15 to 25°. The analgesic effect was very positive and tolerance was good.

Observation 2

Mr. H — 21 years old — Pseudoarthrosis of the knee.

Treatment with the active ingredient of Example 13 in doses of five 100 mg tablets per day for 8 days gave good relief of pain for three hours and a very good antiinflammatory effect. Tolerance was perfect.

Observation 3

Mrs. F — 47 years old — Stripping of varicose veins from the left leg.

Treatment with the active ingredient of Example 13 in doses of six 100 mg tablets per day for 5 days gave complete relief, which became apparent less than 30 minutes after administration and lasted for 3 hours. Tolerance was very good.

Observation 4

Mr. R. — 35 years old — Sciatica of the radicular type on the right side.

Treatment with the active ingredient of Example 13 in doses of four 100 mg tablets per day for 10 days gave an improvement in the results of the Lasegue test from 45 to 75°. The analgesic effect was excellent and tolerance complete.

Observation 5

Mrs. M. — 48 years old — Intense cervical pain from an arthritic spine.

A dose of four 100 mg tablets containing the active ingredient of Example 13 per day for 8 days restored movement to normal amplitude in the neck unaccompanied by pain. The analgesic effect was good and tolerance was very good.

Among the observations made during clinical trials of the compound of Example 22 may be mentioned the following five:

Observation 1

Mr. J. — 79 years old — Intense pain in the neck and arm on the right side.

Treatment with four 150 mg tablets containing the active ingredient of Example 22 per day for eight days gave very good results against pain and signs of inflammation. Tolerance was complete.

Observation 2

Mr. S. — 42 years old — Very intense lumbar pain.

Treatment with the active ingredient of Example 22 in a dose of four 150 mg tablets per day for ten days brought about a very pronounced improvement, the distance which the patient could move his fingertips towards the ground diminishing from 40 to 5 cm. The antalgic effect was excellent and tolerance was complete.

Observation 3

Mr. M. — 62 year old — Inflammation of the arteries in the lower limbs.

Treatment with the active ingredient of Example 22 in a dose of four 150 mg tablets per day for five days gives very distinct relief less than 30 minutes after administration which relief lasted for more than three hours. Tolerance was satisfactory.

Observation 4

Mr. B. — 24 years old — Removal of the left kneecap.

Treatment with the compound of Example 22 at a dosage of six 150 mg tablets per day for 5 days produced relief which was complete, quick (appearing in less than 30 minutes) and long lasting (longer than 3 hours). Tolerance was good.

Observation 5

Mrs. C. — 56 years old — lumbar arthrosis with pain in both hips.

The compound of Example 22, taken at the rate of six 150 mg tablets per day for 10 days brought about an appreciable functional improvement and relief which made its appearance thirty minutes after administration and lasted for three hours. Tolerance was complete.

The following Examples illustrate the preparation of the compounds of the present invention.

EXAMPLE 1

6-[2-(4'-Chlorophenyl)chromonyl] acetic acid

This may be prepared by method A by way of the following intermediates:

(a) 2'-Hydroxy-5'-methyl-4"-chlorodibenzoylmethane

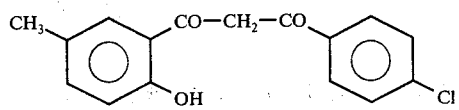

Empirical formula $C_{16}H_{13}ClO_3$: Molecular weight = 288.5

Into a dry reaction vessel are placed 32 g (0.66 mole) of 50% sodium hydride in mineral oil, 200 ml of anhydrous benzene, and 61.5 g (0.33 mole) of ethyl parachlorobenzoate. The mixture is refluxed and over a period of three hours a solution of 33.3 g (0.22 mole) of 5-methyl-2-hydroxyacetophenone in 100 ml of dry benzene is added drop by drop. Reflux is continued for three hours after the addition has been completed. The reaction mixture is cooled using an ice bath and 50 ml of ethanol is added. The solvents are evaporated under reduced pressure using an aspirator on a water bath. The pasty residue is dissolved in 400 ml of 30% acetic acid for an hour while stirring. The product is filtered and dried and the dibenzoylmethane obtained is recrystallised from 100 ml of ethanol.

Melting point = 136°–7° Yield = 27.8 g = 44% (Theoretical yield = 63.3 g).

(b) 6-Methyl-2-(p-chlorophenyl)chromone

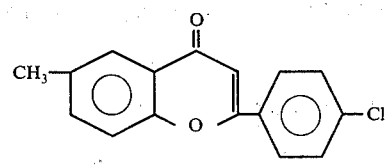

Empirical formula $C_{16}H_{11}O_2Cl$: Molecular weight = 270.5

22.5 g (0.095 mole) of the above dibenzoylmethane, 225 ml of glacial acetic acid, and 22.5 ml of concentrated sulphuric acid are placed in a flask. The mixture is refluxed for one hour, cooled and poured into 800 ml of iced water. The white solid is filtered, washed with water and at once recrystallised from alcohol.

Melting point = 190° C Yield 32 15.5g = 73% (Theoretical yield = 21.1 g)

(c) 6-Bromomethyl-2-p-chlorophenylchromone

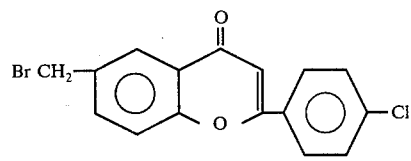

Empirical formula $C_{16}H_{10}BrClO_2$: Molecular weight = 361.5

17.5 g (0.065 mole) of 6-methyl-2-(p-chlorophenyl) chromone, 11.6 g (0.065 mole) of N-bromosuccinimide, 700 ml of carbon tetrachloride, and 0.1 of g of azobisisobutyronitrile are refluxed for 6 hours while stirring. The solvents are evaporated and the solid residue is recrystallised from ethyl acetate.

Melting point = 198° C Yield = 8.8g = 39% (Theoretical yield = 22.75 g)

(d) 6-Cyanomethyl-2-(p-chlorophenyl)chromone

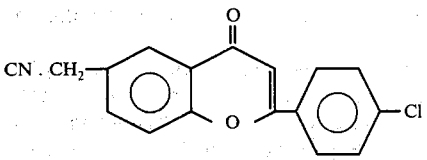

Empirical formula $C_{17}H_{10}ClNO_2$ Molecular weight = 295.71

3.2 g (0.05 mole) of potassium cyanide dissolved in 50 ml of water is placed in a reaction vessel. The solution is heated to 60° C and a solution of 8.3 g (0.023 mole) of 6-bromomethyl-2-(p-chlorophenyl)chromone in 1600 ml of ethanol is added in four portions, one every 20 minutes. Once the addition is complete the mixture is refluxed for 3 hours, evaporated to dryness and dissolved in water. The solid is filtered off and recrystallised from alcohol.

Yield = 5 g = 72% (Theoretical yield = 7 g) M.pt. = 213° C

| Analysis by weight | Calculated | Found |
|---|---|---|
| C% | 69.03 | 69.05 |
| H% | 3.43 | 3.40 |
| N% | 4.75 | 4.73 |

(e) 6-(2-p-Chlorophenylchromonyl) acetic acid

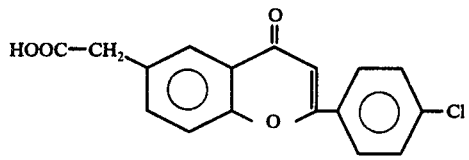

Empirical formula $C_{17}H_{11}ClO_4$: Molecular weight = 314.72

A solution of 4.7 g (0.015 mole) of 2-(p-chlorophenyl)6-cyanomethylchromone, 10 ml of concentrated sulphuric acid, 10 ml of water, and 10 m of glacial acetic acid is refluxed for 2 hours while stirring. The mixture is poured into 60 ml of iced water. The desired acid precipitates. It is purified by formation of its sodium salt and recrystallisation from dioxane. It is a white solid. Yield 3 g = 65% M.Pt. = 242° C Theoretical yield = 5.4 g

| Analysis | Calculated | Found |
|---|---|---|
| C% | 64.88 | 64.85 |
| H% | 3.52 | 3.58 |

EXAMPLE 2

6-(2-o-Chlorophenylchromonyl) acetic acid

This can be prepared by method B utilising the following intermediates:

(a)
2''-Chloro-2'-hydroxymethoxy-5'-methyldibenzoylmethane

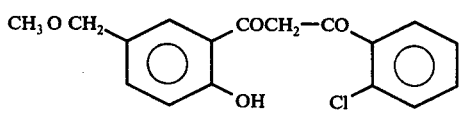

Empirical formula $C_{17}H_{15}ClO_4$: Molecular weight = 318.5

This is prepared from 5-methoxymethyl-2-hydroxyacetophenone, which in turn is prepared from 5-chloromethyl-2-hydroxyacetophenone, in the following manner: 1660 g (9 mole) of 5-chloromethyl-2-hydroxyacetophenone, 13.5 liters of methanol and 940 ml of concentrated hydrochloric acid are refluxed whilst being stirred vigorously. During two hours 1512 g (27 gr. atoms) of powdered 98% iron is added. Reflux is continued for 1½ hours and the mixture allowed to stand overnight. The iron is filtered off and the solution concentrated to 5 liters. It is rendered neutral with 1800 g of sodium bicarbonate dissolved in 10 liters of water. The resulting reaction mixture is extracted with 10.5 liters of benzene and the benzene evaporated under reduced pressure. The product is isolated by distillation.

A colourless oil is obtained B.pt. 100° to 103° C/$_{0.3}$ mm Yield 1232 g = 72% (Theoretical yield = 1620 g)

By operating as described in Example 1a, and using the noted quantities, condensation with ethyl-o-chlorobenzoate is effected: 32 g (0.66 mole) of 50% sodium hydride in mineral oil, 36.5 g (0.20 mole) of ethyl o-chlorobenzoate, 23 g (0.13 mole) of 2-hydroxymethoxy-5-methylacetophenone, and 225 ml of anhydrous benzene. The dibenzoylmethane is isolated in solution in 30% acetic acid and is purified by recrystallisation from 200 ml of isopropanol.

A yellow solid is obtained M.pt = 95° C Yield = 26.3 g = 62% (Theoretical yield = 42.5 g)

(b) 6-Bromomethyl-2-(o-chlorophenyl)chromone

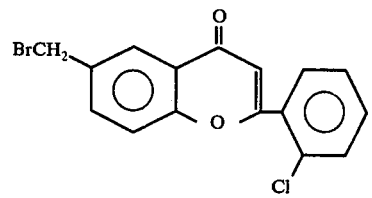

Empirical formula $C_{16}H_{10}Br\ Cl\ O_2$: Molecular weight = 349.62

26 g (0.082 mole) of 2''-chloro-2'-hydroxy-5'-methoxymethyldibenzoylmethane, 78 ml of 66% hydrobromic acid and 104 ml of glacial acetic acid are refluxed for three hours. The reaction mixture is poured into iced water and the solid which separates is filtered. It is then washed with water and recrystallised from acetone. Yield: 17.4 g = 63% (Theoretical yield = 28.5 g). M.pt = 91° C.

| Analysis | Calculated | Found |
|---|---|---|
| C% | 54.97 | 54.94 |
| H% | 2.88 | 2.90 |
| Br% | 22.86 | 22.82 |

(c) 2-(o-Chlorophenyl)-6-cyanomethylchromone

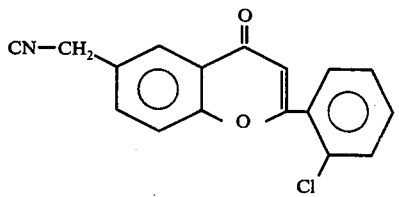

Empirical formula $C_{17}H_{10}Cl\ NO_2$: Molecular weight = 295.71

This is prepared by method A, Example 1(d) using the following materials:

5 g (0.0143 mole) of 6-bromomethyl-2-(o-chlorophenyl)chromone, 1.56 g (0.0286 mole) of potassium cyanide, 200 ml of ethanol and 10 ml of water. A white solid is obtained which is recrystallised from 50 ml of ethanol. Yield: 3.3 g = 66% (Theoretical yield = 4.3 g) M.Pt 131 to 132° C

| Analysis | Calculated | Found |
|---|---|---|
| C% | 69.05 | 69.01 |
| H% | 3.40 | 3.43 |
| M% | 4.73 | 4.77 |
| Cl% | 11.99 | 12.03 |

(d) 6-(2-o-Chlorophenylchromonyl) acetic acid

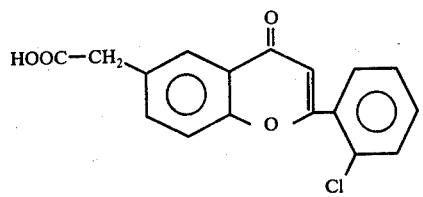

Empirical formula $C_{17}H_{11}Cl\ O_4$: Molecular weight = 314.72

A mixture of 29.5 g (0.1 mole) of 2-(o-chlorophenyl)-6-cyanomethylchromone, 68 ml of glacial acetic acid and 68 ml of water is refluxed for three hours. The reaction mixture is poured into 800 ml of iced water and the solid which separates is filtered. It is then dissolved in 700 ml of hot 5% sodium bicarbonate solution, filtered, and acidified with 3N hydrochloric acid. It is then recrystallised from ethyl alcohol.

A white solid is obtained. M.pt = 217° to 218° C. Yield 27 g = 90% (Theoretical yield 32 31.4 g)

| Analysis | Calculated | Found |
|---|---|---|
| C% | 64.88 | 64.90 |
| H% | 3.52 | 3.56 |
| Cl% | 11.27 | 11.29 |

EXAMPLE 3

6-(2-m-(Chlorophenyl)chromonyl)acetic acid

This is prepared by the same procedure as that used in Example 2. The following intermediates are isolated:

(a) 3''-Chloro-2'-hydroxy-5'-methoxymethyldibenzoylmethane

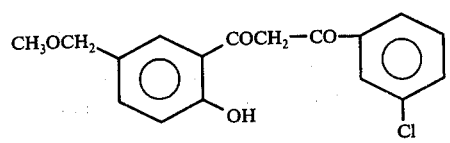

Empirical formula $C_{15}H_7Cl\ O_4$: Molecular weight = 318.5: A yellow solid is obtained. M.pt = 86° C: Yield = 44%

(b) 6-Bromethyl-2-(m-chlorophenyl)-chromone

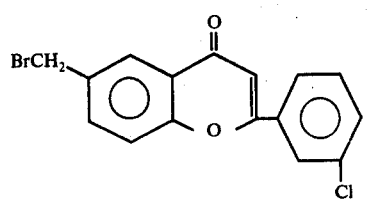

Empirical formula $C_{16}H_{10}Br\ Cl\ O_2$: Molecular weight = 349.52 A white solid is obtained. M.pt = 162° C (acetone): Yield = 71%

(c) 2-(m-Chlorophenyl)-6-cyanomethylchromone

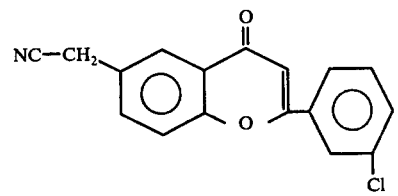

Empirical formula $C_{17}H_{10}Cl\ NO_2$: Molecular weight = 295.71: A white solid is obtained. M.pt = 195°-6° C (ethanol): Yield = 56%.

| Analysis | Calculated | Found |
|---|---|---|
| C% | 69.05 | 69.02 |
| H% | 3.40 | 3.40 |
| N% | 4.73 | 4.75 |

(d) 6-(2-m-Chlorophenylchromonyl) acetic acid

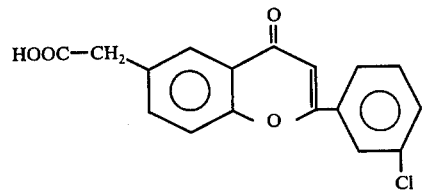

Empirical formula $C_{17}H_{11}Cl\ O_4$: Molecular weight = 314.72: A white solid is obtained. M.pt = 208° C (ethanol): Yield 54%.

| Analysis | Calculated | Found |
|---|---|---|
| C% | 64.88 | 64.85 |
| H% | 3.53 | 3.50 |
| Cl% | 11.27 | 11.30 |

EXAMPLE 4

6-(m-Trifluoromethyl-2-phenylchromonyl)acetic acid

This is prepared by Method B. The following intermediates are isolated:

(a)
2'-Hydroxy-5'-methoxymethyl-3"-trifluoromethyl-dibenzoylmethane

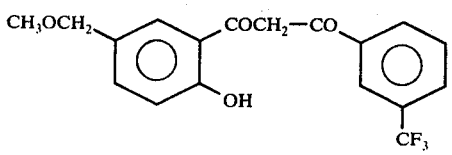

Empirical formula $C_{18}H_{14}F_3O_4$: Molecular weight = 351: A yellow solid is obtained. M.pt = 128° C (ethanol): Yield = 73%.

(b)
6-Bromomethyl-2-m-trifluoromethyl-phenylchromone

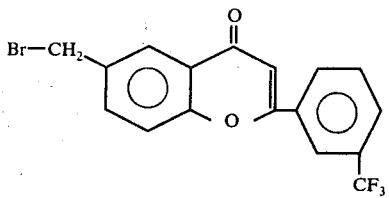

Empirical formula $C_{17}H_{10}BrF_3O_2$: Molecular weight = 383. A beige solid. M.pt = 168° C (acetone): Yield = 72%.

(c) 6-Cyanomethyl-2-trifluoromethylphenylchromone

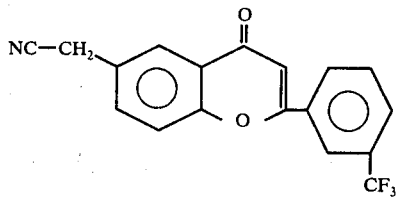

Empirical formula $C_{18}H_{10}F_3NO_2$: Molecular weight = 329: A white solid. M.pt = 152° C (ethanol) Yield = 36%.

(d) 6-(2'-m-Trifluoromethylphenyl)-chromonyl)acetic acid

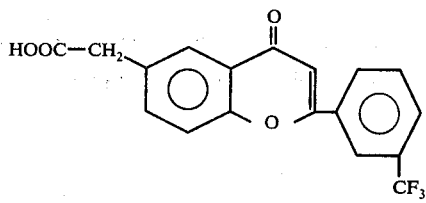

Empirical formula $C_{18}H_{11}F_3O_4$: Molecular weight = 348.29: A white solid. M.pt = 195° C (ethanol): Yield: 52%.

| Analysis | Calculated | Found |
|---|---|---|
| C% | 62.08 | 62.05 |
| H% | 3.18 | 3.21 |
| F% | 16.36 | 16.39 |

EXAMPLE 5
6-(2-p-Fluorophenylchromonyl)acetic acid

This is prepared by method B as described in Example 2, with production of the following intermediates:

(a)
4"-Fluoro-2'-hydroxy-5-methoxymethyldibenzoylmethane

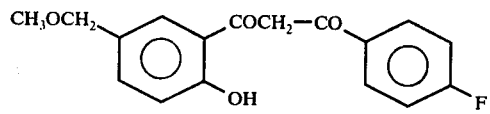

Empirical formula $C_{17}H_{15}FO_4$: Molecular weight = 303. A yellow solid. M.pt = 108° C (di-isopropyl ether). Yield = 50%.

(b) 5-Bromomethyl-2-(p-fluorophenyl)chromone

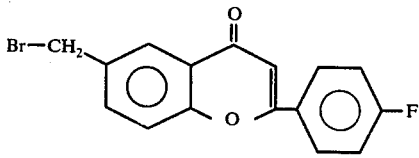

Empirical formula $C_{16}H_{10}Br FO_2$: Molecular weight = 333.17. A white solid. M.pt = 151° C (acetone): Yield = 45%.

| | Calculated | Found |
|---|---|---|
| C% | 57.68 | 57.73 |
| H% | 3.02 | 3.04 |
| Br% | 23.09 | 24.05 |
| F% | 5.70 | 5.73 |

(c) 6-Cyanomethyl-2-p-fluorophenylchromone

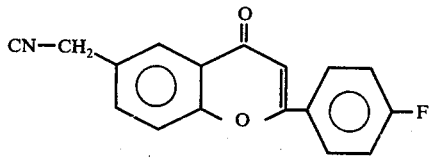

Empirical formula $C_{17}H_{10}NFO_2$: Molecular weight = 279. A white solid. M.pt = 206° C (ethanol). Yield = 54%.

(d) 6-(2-p-Fluorophenylchromonyl)acetic acid

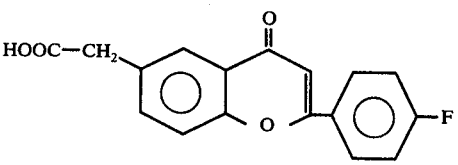

Empirical formula $C_{17}H_{11}FO_4$: Molecular weight = 298.27. A white solid. M.pt = 225° C (ethanol). Yield = 80%.

| Analysis | Calculated | Found |
|---|---|---|
| C% | 68.45 | 68.48 |
| H% | 3.71 | 3.80 |

| Analysis | Calculated | Found |
|---|---|---|
| Tr% | 6.37 | 6.39 |

EXAMPLE 6

6-[2-(2'-thienyl)chromonyl]acetic acid

Preparation is carried out by the method used in Example 2. The following intermediates are obtained:

(a) 1-(2'-Hydroxy-5'-methoxymethylphenyl)-3-(2''-thienyl)-1,3-dioxopropane

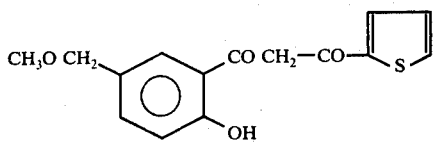

Empirical formula $C_{15}H_{14}SO_4$. Molecular weight = 290. A white solid. M.pt = 90° C (isopropanol). Yield = 50%.

(b) 6-Bromomethyl-2-(α-thienyl)chromone

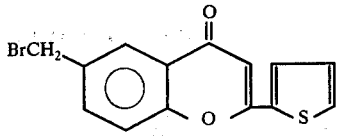

Empirical formula $C_{14}H_9BrO_2S$. Molecular weight = 321. A white solid. M.pt = 179° C (acetone). Yield = 42%.

(c) 6-Cyanomethyl-2-(α-thienyl)chromone

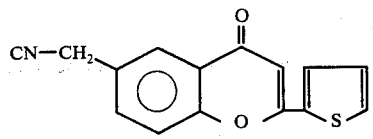

Empirical formula $C_{15}H_9O_2NS$. Molecular weight = 267.311. A white solid. M.pt = 202° C (from ethanol-dioxan 7:3). Yield = 68%.

(d) 6-[2-(2'-Thienyl)chromonyl]acetic acid

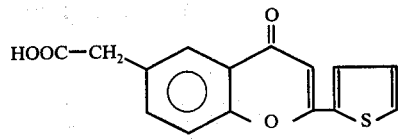

Empirical formula $C_{15}H_{10}SO_4$. Molecular weight = 286.311. A white solid. M.pt. = 205° C (ethanol). Yield = 73%.

| Analysis | Calculated | Found |
|---|---|---|
| C% | 62.92 | 62.86 |
| H% | 3.52 | 3.59 |
| Tr% | 11.20 | 11.23 |

EXAMPLE 7

6-[2-(2'-furyl)chromonyl]acetic acid

This is prepared by method B used in Example 2. The following intermediates are obtained:

(a) 1-(2'-Hydroxy-5'-methoxymethylphenyl)-3-(2''-furyl)-1,3-dioxopropane

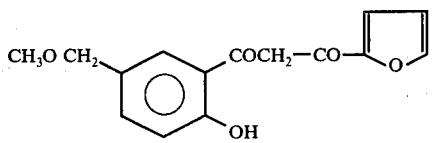

Empirical formula $C_{15}H_{14}O_5$. Molecular weight = 274. A yellow solid. M.pt = 73° C (hexane). Yield = 73%.

(b) 6-Bromomethyl-2-(2'-furyl)chromone

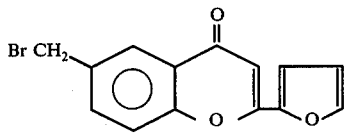

Empirical formula $C_{14}H_9BrO_2$. Molecular weight = 289. A white solid. M.pt = 184° C (ethanol). Yield = 56%.

(c) 6-Cyanomethyl-2-(2'-furyl)-chromone

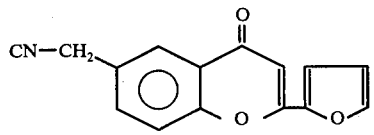

Empirical formula $C_{15}H_9NO_2$. Molecular weight = 251. A white solid. M.pt 210° C (ethanol). Yield = 50%.

(d) 6-[2-(2'-furyl)chromonyl]acetic acid

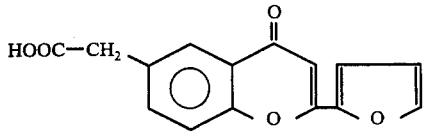

Empirical formula $C_{15}H_{10}O_5$. Molecular weight = 270.25. A white solid. M.pt = 198° C (ethanol). Yield = 65%.

| Analysis | Calculated | Found |
|---|---|---|
| C% | 66.66 | 66.69 |
| H% | 3.73 | 3.68 |

EXAMPLE 8

6-(2-Methylchromonyl)acetic acid

This is prepared by the method illustrated in Example 2. The following intermediates are obtained:

(a) 1-(2'-Hydroxy-5'-methoxymethylphenyl)-1,3-dioxobutane

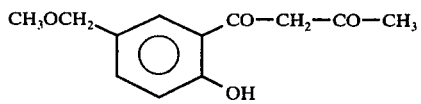

Empirical formula $C_{12}H_{14}O_4$. Molecular weight —. A light yellow solid. M.pt = 89° C (di-isopropylether) Yield = 30%.

(b) 6-Bromomethyl-2-methylchromone

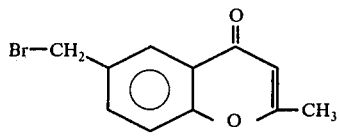

Empirical formula $C_{11}H_9O_2Br$. Molecular weight = 253. A white solid. M.pt = 132° C (ethanol-water 1:1).

(c) 6-Cyanomethyl-2-methylchromone

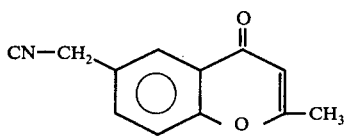

Empirical formula $C_{12}H_9O_2N$. Molecular weight = 199. A white solid. M.pt = 122° C (isopropanol). Yield = 53%.

(d) 6-(2-Methylchromonyl)acetic acid

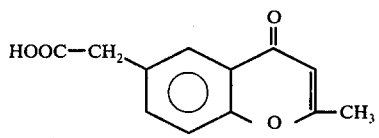

Empirical formula $C_{12}H_{10}O_4$. Molecular weight 218.212. A white solid. M.pt = 192° (ethanol). Yield = 51%.

| Analysis | Calculated | Found |
|---|---|---|
| C% | 66.05 | 65.99 |
| H% | 4.62 | 4.65 |

EXAMPLE 9

6-[2-(3'-Thienyl)chromonyl]acetic acid

This is prepared by the method illustrated in Example 2. The following intermediates were isolated:

(a) 1-(2'-Hydroxy-5'-methoxymethylphenyl)-3-(3''-thienyl)-1,3-dioxopropane

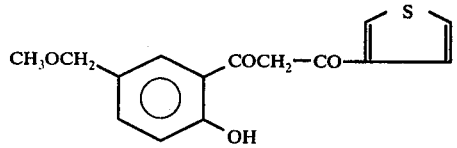

Empirical formula $C_{15}H_{14}SO_4$. Molecular weight = 290. A yellowish solid, which is not purified but is used in its crude state to make (b).

(b) 6-Bromomethyl-2-(β-thienyl)chromone

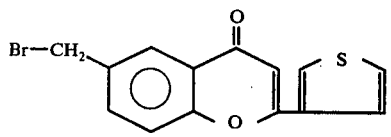

Empirical formula $C_{14}H_9BrO_2S$. Molecular weight 321. A white solid. M.pt = 160° C (ethanol). Yield = 321.

(c) 6-Cyanomethyl-2-(β-thienyl)chromone

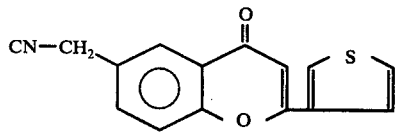

Empirical formula $C_{15}H_9O_2NS$. Molecular weight = 267.319 A white solid. M.pt 192° C (washed in ethanol). Yield = 74%.

(d) 6-[2-(3'-Thienyl)chromonyl]acetic acid

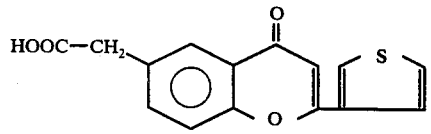

Empirical formula $C_{15}H_{10}O_4S$. Molecular weight = 286.311. A white solid. M.pt 207°-8° C (ethanol). Yield = 30%.

| Analysis | Calculated | Found |
|---|---|---|
| C% | 62.92 | 62.86 |
| H% | 3.52 | 3.48 |
| S% | 11.20 | 11.18 |

EXAMPLE 10

6-[2-[2'-(5'-Chlorothienyl]chromonyl]acetic acid

This is prepared as described in Example 2. The following intermediates were isolated:

(a) 1-(2′-Hydroxy-5′-methoxymethylphenyl)-3-[2″-(5″-chlorothienyl)]-1,3-dioxopropane

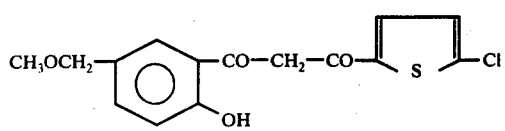

Empirical formula $C_{15}H_{13}O_4SCl$. Molecular weight = 324.5. A solid. M.pt = 106° C (diisopropylether) Yield = 69%.

(b) 6-Bromomethyl-2-[α-(5′-chlorothienyl)]chromone

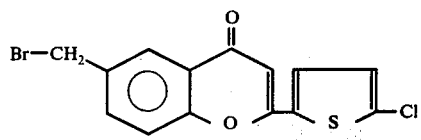

Empirical formula $C_{14}H_8Br\ S\ Cl\ O_3$. Molecular weight = 355.5. A white solid. M.pt = 180° C. Yield 76%.

(c) 6-Cyanomethyl-2-[2′-(5′-chlorothienyl)]chromone

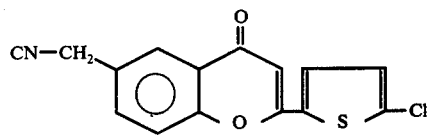

Empirical formula $C_{15}H_8NO_2S$. Molecular weight = 301.5. A white solid. M.pt = 210° C (dioxane). Yield = 50%.

(d) 6-[[2′-(5′-Chlorothienyl-2)]chromonyl]acetic acid

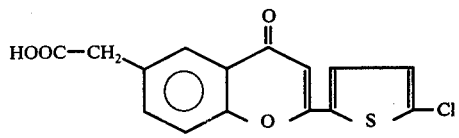

Empirical formula $C_{15}H_9Cl\ O_4\ S$. Molecular weight = 320.74. A white solid. M.pt 226° to 227° C (dioxane) Yield = 70%.

| Analysis | Calculated | Found |
|---|---|---|
| C% | 56.17 | 56.13 |
| H% | 2.82 | 2.99 |
| Cl% | 11.06 | 10.98 |

EXAMPLE 11

Methyl-6-flavonylacetate

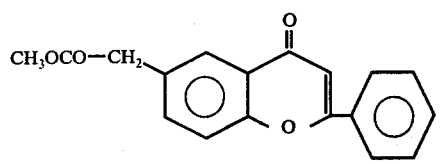

Empirical formula $C_{18}H_{14}O_4$. Molecular weight = 294. 5.2 g (0.0186 mole) of 6-flavonylacetic acid, 3.7 ml of concentrated sulphuric acid, and 70 ml of anhydrous methanol are refluxed for 7 hours. The reaction mixture is poured into 140 ml of iced water. The desired ester crystallises. It is filtered, washed with sodium bicarbonate solution and then with water. Yield = 4,45 g = 81% (Theoretical yield = 5.45 g). M.pt = 117° C (methanol)

| Analysis | Calculated | Found |
|---|---|---|
| C% | 73.45 | 73.48 |
| H% | 4.79 | 4.82 |

EXAMPLE 12

Methyl-6-[2-(2′-thienyl)chromonyl]acetate

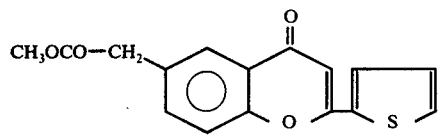

Empirical formula $C_{16}H_{12}SO_4$. Molecular weight = 300.32.

30 g (0.105 mole) of 6-[2-(2′-thienyl)chromonyl]acetic acid, 400 ml of anhydrous methanol and 21 ml of concentrated sulphuric acid are refluxed for 7 hours. The mixture is cooled and poured into one liter of water. The precipitate obtained is filtered and dried. It is then recrystallised from 200 ml of methanol. Yield = 25.8 g = 83%. (Theoretical yield = 31.5 g). M.pt = 106°-7° C.

| Analysis | Calculated | Found |
|---|---|---|
| C% | 63.99 | 63.77 |
| H% | 4.02 | 4.28 |
| S% | 10.68 | 10.69 |

EXAMPLE 13

2-[2′-(α-Thienyl)-6′-chromonyl]propionic acid (a) Ethyl 2-(2′-[α-thienyl]-6′-chromonyl)-2-methylmalonate

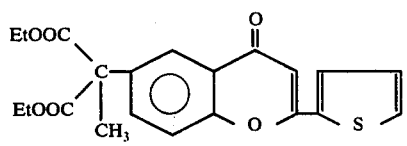

Empirical formula $C_{21}H_{20}O_6S$. Molecular weight = 400.23.

A suspension of 8.8 g (0.27 mole) of 72% sodium hydride in mineral oil is heated to boiling with 550 ml of ethyl carbonate whilst being stirred. 73.5 g (0.245 mole) of methyl-6-[2-(α-thienyl)chromonyl] acetate (Example 12) is then added drop by drop. When the addition has been completed, reflux is continued for a further 2 hours. The mixture is then cooled to 20° C and a solution of 83 g (0.6 mole) of methyl iodide in 240 ml of dimethylformamide is quickly added. The reaction mixture is stirred for 12 hours at ambient temperature and the solvents are then evaporated under reduced pressure.

The residue is dissolved in water and extracted with benzene. The organic phase is separated, then dried and the benzene evaporated under reduced pressure and the residual oil crystallised from di-isopropyl ether. Yield = 82%. M.pt = 90° C (di-isopropyl ether).

| Analysis | Calculated | Found |
|---|---|---|
| C% | 63.00 | 62.75 |
| H% | 5.03 | 4.95 |
| S% | 8.00 | 7.90 |

NMR (deuterochloroform), δ (ppm) with reference to tetramethylsilane 6 H at 1.35 (triplet J = 7 cps), 3 H at 2 (singlet), 4 H at 4.35 (quartet J = 7 cps), 1 H at 6.8 (singlet), 6 H from 7.1 to 8.4 (multiplet).

(b) 2-[2'-(α-Thienyl)-6'-chromonyl]propionic acid

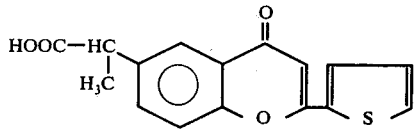

Empirical formula $C_{16}H_{12}SO_4$. Molecular weight = 300.31.

A solution of 80 g (0.2 mole) of ethyl-2-[2'-(α-thienyl)-6'-chromonyl]-2-methyl malonate in 400 ml of acetic acid and 200 ml of concentrated hydrochloric acid is refluxed for 7 hours.

The solution is cooled to 10° C and the acid obtained is filtered. It is then washed with water and purified by being dissolved in hot sodium bicarbonate solution and refluxing with animal black. The product is filtered and acidified with concentrated hydrochloric acid. The acid is then filtered and at once crystallised from acetic acid. A light yellow solid is obtained. Yield = 75%. M.pt = 255°–260° C.

| Analysis | Calculated | Found |
|---|---|---|
| C% | 63.98 | 64.09 |
| H% | 4.03 | 4.03 |
| S% | 10.68 | 10.69 |

NMR (DMSO d₆ δ (ppm) with reference to tetramethylsilane, 3 H at 1.5 (doublet J = 7 cps), 1 H at 3.95 (quartet J = 7 cps), 1 H at 7 (singlet), 1 H from 7.25 to 7.50 (multiplet), 2 H from 7.75 to 7.90 (multiplet), 2 H from 8 to 8.25 (multiplet), 1 H from 12 to 13 (broad spread).

EXAMPLE 14

2-[2'-(α-furyl)-6'-chromonyl]propionic acid (a) Methyl 6-[2-(α-furyl)-chromonyl]acetate

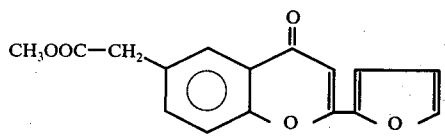

Empirical formula $C_{16}H_{12}O_5$. Molecular weight = 284.26.

A solution of 14.4 g (0.053 mole) of 6-[2-(2'-furyl)-chromonyl]acetic acid (Example 7) in 200 ml of anhydrous methanol and 12 ml of concentrated sulphuric acid is refluxed for 8 hours. The solution is then cooled and poured into water. The precipitate obtained is filtered, dried and recrystallised. Yield = 70%. M.pt = 117° C (methanol).

| Analysis | Calculated | Found |
|---|---|---|
| C% | 67.62 | 67.45 |
| H% | 4.25 | 4.15 |

(b) Ethyl 2-[6-(2-α-Furylchromonyl)]-2-methylmalonate

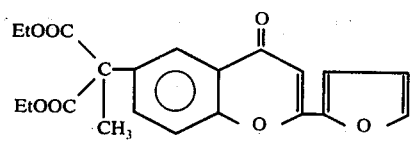

Empirical formula $C_{21}H_{20}O_7$. Molecular weight = 384.37.

This is prepared as described under (a) of Example 13 from the above acetate. A light yellow solid is obtained. Yield = 70%. M.pt = 88° C (di-isopropyl ether).

| Analysis | Calculated | Found |
|---|---|---|
| C% | 65.62 | 65.80 |
| H% | 5.24 | 5.15 |

RMN (deuterochloroform) δ (ppm) with reference to tetramethylsilane, 6 H at 1.3 (triplet J = 7 cps), 3 H at 2 (singlet), 4 H at 4.3 (quartet J = 7 cps), 1 H from 6.55 to 6.7 (multiplet), 1 H at 6.75 (singlet), 5 H from 7.1 to 8.4 (multiplet).

(c) 2-[2'-(α-Furyl)-6'-chromonyl]propionic acid

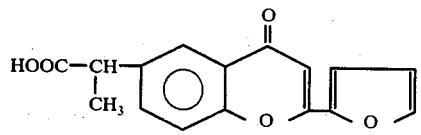

Empirical formula $C_{16}H_{12}O_5$. Molecular weight = 284.26.

A solution of 5.5 g (0.0143 mole) of ethyl 2-[2-(α-furyl)-6-chromonyl]-2-methylmalonate in 28 ml of acetic acid and 14 ml of hydrochloric acid is refluxed for 7 hours. Separation and purification are described under Example 13(b), and a white solid is obtained. Yield = 60%. M.pt = 210°–215° C (isopropanol).

| Analysis | Calculated | Found |
|---|---|---|
| C% | 67.60 | 67.57 |
| H% | 4.25 | 4.25 |

NMR (DMSO d₆ δ (ppm) with reference to tetramethylsilane, 3 H at 1.5 (doublet J = 7 cps), 1 H at 4 (quartet J = 7 cps), 1 H at 6.65 (singlet), 1 H from 6.8 to 7 (multiplet), 5 H from 7.5 to 8.2 (multiplet), 1 H from 12.4 to 13 (spread).

EXAMPLE 15

2-[2'-(β-Thienyl)-6'-chromonyl]propionic acid (a) Methyl [2'-(β-Thienyl)-6'-chromonyl]acetate

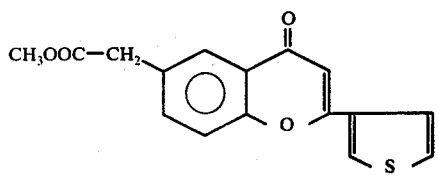

Empirical formula C$_{16}$H$_{12}$O$_4$S. Molecular weight = 300.38.

This is prepared as described under Example 14(a). A white solid is obtained. Yield = 93%. M.pt = 111° C.

NMR (deuterochloroform δ (ppm) with reference to tetramethylsilane, 5 H at 3.8 (singlet), 1 H at 6.8 (singlet), 6 H from 7.4 to 8.3 (multiplet).

(b) Ethyl 2-[2'-(β-Thienyl)-6'-chromonyl]-2-methyl malonate

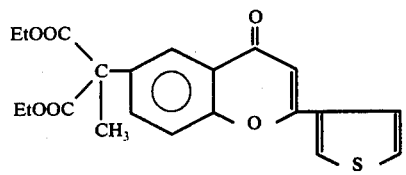

Empirical formula C$_{21}$H$_{20}$O$_6$S. Molecular weight = 400.4.

This is prepared as described under Example 13(a), starting from methyl [2'-(β-thienyl)-6'-chromonyl]acetate. A white solid is obtained. Yield = 60%. M.pt = 95° C.

| Analysis | Calculated | Found |
|---|---|---|
| C% | 63.00 | 62.83 |
| H% | 5.03 | 4.92 |
| S% | 8.00 | 8.10 |

NMR (deuterochloroform) δ (ppm) with reference to tetramethylsilane, 6 H at 1.35 (triplet J = 7 cps), 3 H at 2 (singlet), 4 H at 4.4 (quartet J = 7 cps), 1 H at 6.8 (singlet), 6 H from 7.3 to 8.5 (multiplet).

(c) 2-[2'-(β-Thienyl)-6'-chromonyl]propionic acid

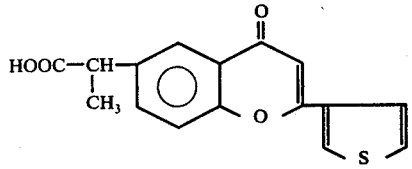

Empirical formula C$_{16}$H$_{12}$SO$_4$. Molecular weight = 300.31.

This is prepared as described in Example 13(b) from the corresponding malonic ester. A light yellow solid is obtained. Yield = 70%. M.pt = 215°–218° C.

| Analysis | Calculated | Found |
|---|---|---|
| C% | 63.98 | 64.11 |
| H% | 4.03 | 4.12 |
| S% | 10.68 | 10.74 |

NMR (DMSO d$_6$) δ (ppm) with reference to tetramethylsilane, 3 H at 1.5 (triplet J = 7 cps), 1 H at 3.95 (quartet J = 7 cps), 1 H at 7 (singlet), 6 H from 7.65 to 8.65 (multiplet), 1 H from 12.4 to 13 (spread).

EXAMPLE 16

2-[2'-(p-Chlorophenyl)-6'-chromonyl]propionic acid (a) Methyl [2'-(p-chlorophenyl)-6'-chromonyl]acetate

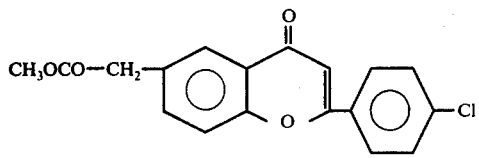

Empirical formula C$_{18}$H$_{13}$ClO$_4$. Molecular weight = 318.5.

A solution of 105 g (0.344 mole) of 6-[2-(p-chlorophenyl)-6'-chromonyl]acetic acid (Example 1) in 1400 ml of anhydrous methanol and 70 ml of concentrated sulphuric acid is refluxed for 6 hours. The solution is filtered and allowed to stand overnight at −20° C.

A solid separates and is filtered and is immediately recrystallised from 2800 ml of methanol. A white solid is obtained. Yield 85%. M.pt 135°–137° C.

(b) Ethyl 2-[2'-(p-Chlorophenyl)-6'-chromonyl]-2-methylmalonate

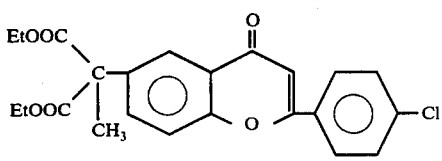

Empirical formula C$_{23}$H$_{21}$ClO$_6$. Molecular weight 428.872.

A suspension of 3.47 g (0.0725 mole) of 50% sodium hydride in mineral oil in 200 ml of ethyl carbonate is heated to 50° C whilst being stirred and 22 g (0.069 mole) of methyl (2'-p-chlorophenyl-6'-chromonyl)acetate is slowly added thereto. The mixture is then refluxed for 2 hours. It is cooled to ambient temperature and a solution of 23.5 g (0.165 mole) of methyl iodide in 68 ml of dimethyl formamide is added drop by drop. The mixture is stirred for 48 hours at 20° C. An abundant precipitate separates out. The precipitate is filtered off and the mother liquor is evaporated to dryness.

The solid and the dry residue are admixed, washed with water and extracted with benzene. The benzene extract is dried and the solvent evaporated under reduced pressure. The yellowish solid residue is recrystallised from di-isopropyl ether. Yield = 75%. M.pt = 140° C.

| Analysis | Calculated | Found |
|---|---|---|
| C% | 64.41 | 64.22 |
| H% | 4.93 | 4.85 |

| Analysis | Calculated | Found |
|---|---|---|
| Cl% | 8.26 | 8.15 |

NMR (deuterochloroform) δ (ppm) with reference to tetramethylsilane, 6 H at 1.3 (triplet J = 7 cps), 3 H at 2 (singlet), 4 H at 4.3 (quartet J = 7), 1 H at 6.85 (singlet), 7 H from 7.4 to 8.4 (multiplet).

(c) 2-[2'-(p-Chlorophenyl)-6'-chromonyl]propionic acid

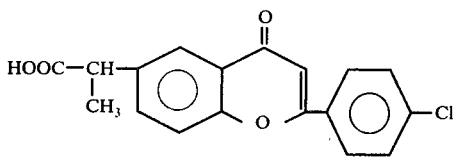

Empirical formula $C_{18}H_{13}O_4Cl$. Molecular weight = 328.737.

A solution of 22 g (0.07 mole) of ethyl 2-[2'-(p-chlorophenyl)-6'-chromonyl]-2-methyl malonate in 120 ml of glacial acetic acid and 60 ml of concentrated hydrochloric acid is refluxed for 6 hours. The reaction mixture is then poured into water and the solid obtained is filtered. The solid is then dissolved in 1000 ml of a 5% solution of sodium bicarbonate, and the solution is washed with benzene, separated and made acid. Recrystallisation is from isopropanol or toluene. Yield = 60%. M.pt = 184°–185° C.

| Analysis | Calculated | Found |
|---|---|---|
| C% | 65.76 | 65.91 |
| H% | 3.99 | 4.03 |
| Cl% | 10.78 | 10.71 |

NMR (DMSO d$_6$) δ (ppm) with reference to tetramethylsilane, 3 H at 1.5 (doublet J = 7 cps), 1 H at 3.95 (quartet J = 7 cps), 1 H at 7.1 (singlet), 7 H from 7.5 to 8.4 (spread), 1 H from 12.1 to 12.5 (spread peaking at 12.3).

EXAMPLE 17

2-[2'-(o-Chlorophenyl)-6'-chromonyl]propionic acid (a) Methyl [2'-(o-chlorophenyl)-6'-chromonyl]acetate

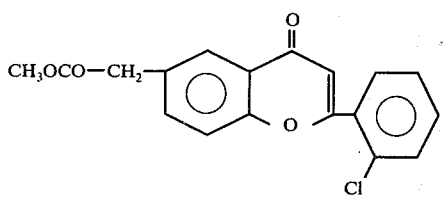

Empirical formula $C_{18}H_{13}Cl\ O_4$. Molecular weight = 318.5.

This is prepared as described in Example 16(a) from 6-[2-(o-chlorophenyl chromonyl]acetic acid (Example 2). An oily product is obtained which is difficult to crystallise.

NMR (carbon tetrachloride) δ (ppm) with reference to tetramethylsilane, 5 H at 3.7 (singlet), 1 H at 6.5 (singlet), 7 H from 7.3 to 8.1 (spread).

(b) Ethyl 2-[2'-(o-Chlorophenyl)-6-chromonyl]-2-methyl malonate

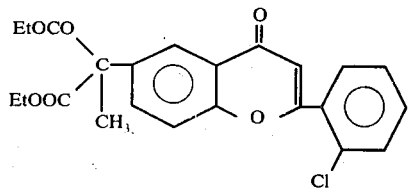

Empirical formula $C_{23}H_{21}ClO_6$. Molecular weight = 428.872.

This is prepared as described in Example 16(b) starting from methyl [2'-(o-chlorophenyl)-6'-chromonyl] acetate. The product obtained is a yellow oil which is difficult to crystallise.

NMR (carbon tetrachloride) δ (ppm) with reference to tetramethylsilane, 5 H at 1.2 (triplet J = 7 cps), 3 H at 1.9 (singlet), 4 H at 4.2 (quartet J = 7 cps), 1 H at 6.55 (singlet), 7 H from 7 to 8.3 (spread).

(c) 2-[2'-(o-Chlorophenyl)-6'-chromonyl]propionic acid

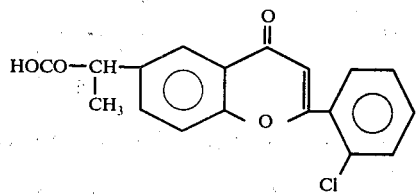

Empirical formula $C_{18}H_{13}O_4Cl$. Molecular weight 328.737.

This is prepared as described in Example 16(c) starting from ethyl 2-[2'-(o-chlorophenyl)-6'-chromonyl]-2-methylmalonate. A white solid is obtained. Yield = 60%. M.pt 194°–196° C (toluene).

| Analysis | Calculated | Found |
|---|---|---|
| C% | 65.76 | 65.88 |
| H% | 3.99 | 4.07 |
| Cl | 10.78 | 10.62 |

NMR (DMSO d$_6$) δ (ppm) with reference to tetramethylsilane, 3 H at 1.55 (doublet J = 7 cps), 1 H at 4.05 (quartet J = 7 cps), 1 H at 6.75 (singlet), 7 H from 7 to 8.4 (spread), 1 H from 12.5 to 13 (spread peaking at 12.75).

EXAMPLE 18

6-[2-(2',4'-Dichlorophenyl)chromonyl]acetic acid (Method B)

This is prepared by method B in the following intermediates:

(a) 2",4"-Dichloro-2'-hydroxy-5'-methoxymethyl dibenzoyl methane

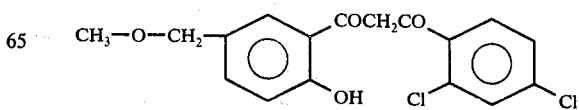

Empirical formula $C_{17}H_{14}Cl_2O_4$. Molecular weight = 353.

71.5 g (1.49 mole) of 50% sodium hydride in mineral oil, 600 ml of dry benzene and 15.7 g (0.745 mole) of ethyl 2,4-dichlorobenzoate are placed in a dry reaction vessel.

While stirring, the mixture is refluxed and during a period of two hours a solution of 89.4 g (0.496 mole) of 2-hydroxy-5-methoxymethylacetophenone in 280 ml of dry benzene is added thereto. The reaction is completed by refluxing for two hours and the mixture cooled to 30° C.

300 ml of ethanol is added and the alcohol/benzene azeotrope is removed under reduced pressure. 2000 ml of 30% acetic acid is added and the whole extracted with benzene. The benzene extracts are united, then dried and the benzene removed under reduced pressure. The solid residue is recrystallised from 1000 ml of a 9:1 mixture of alcohol and water. A yellow solid is isolated. Yield = 86%. M.pt = 96°–100° C.

(b) 6-Bromomethyl-2-(2',4'-dichlorophenyl)chromone

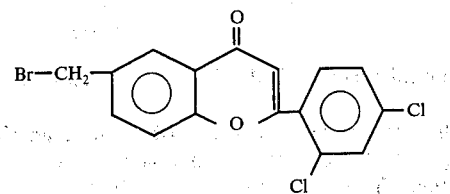

Empirical formula $C_{16}H_9BrCl_2O_2$. Molecular weight = 384.068.

A mixture of 151 g (0.427 mole) of 2'',4'''-dichloro-2'-hydroxy-5'-methoxymethyldibenzoylmethane, 470 ml of 62% HBr and 600 ml of glacial acetic acid is heated to 60° to 70° C for three hours, whilst stirring. The resulting mixture is poured into water, filtered, and the solid which has separated is recrystallised from a mixture of 1700 ml of acetone and 270 ml of dimethylformamide. Yield = 56%. M.pt = 161° to 162° C (acetone).

| Analysis | Calculated | Found |
|---|---|---|
| C% | 49.96 | 49.99 |
| H% | 2.52 | 2.65 |
| Cl% | 18.43 | 18.39 |

(c) 6-Cyanomethyl-2-(2',4'-dichlorophenyl)chromone

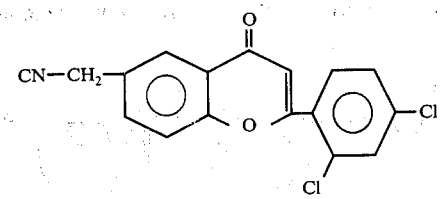

Empirical formula $C_{17}H_9Cl_2NO_2$. Molecular weight = 330.

A solution of 31.2 g (0.48 mole) of 95% potassium cyanide in 250 ml of water is heated to 85° C. A solution of 92 g (0.24 mole) of 6-bromomethyl-2-(2',4'-dichlorophenyl)chromone in 3900 ml of ethanol is added in four portions, one every twenty minutes. The mixture is refluxed for three hours and then evaporated to dryness. The residue is dissolved in 1000 ml of water and filtered.

Recrystallisation is then effected from 2200 ml of a 10:1 mixture of ethanol and dimethylformamide. Yield = 52%. M.pt = 190° C.

NMR (DMSO $d_6$) δ (ppm) with reference to tetramethylsilane, 2 H at 4.35 (singlet), 1 H at 6.80 (singlet), 6 H from 7.4 to 8.7 (spread).

(d) 6-[2-(2',4'-Dichlorophenyl)chromonyl]acetic acid

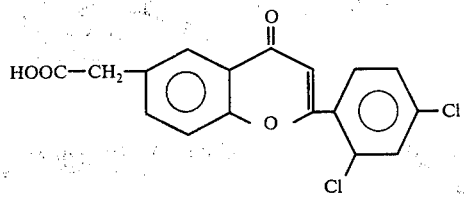

Empirical formula $C_{17}H_{10}Cl_2O_4$. Molecular weight = 349.16.

A solution of 10 g (0.03 mole) of 6-cyanomethyl-2-(2',4'-dichlorophenyl)chromone in a mixture of 25 ml of glacial acetic acid, 25 ml of concentrated sulphuric acid, and 25 ml of water, is refluxed for 3 hours. The solution is then poured into water, filtered, and the acid dissolved in 500 ml of an aqueous 5% solution of sodium bicarbonate.

The solution is filtered, acidified, filtered, and the acid recrystallised from 200 ml of a 12:8 mixture of water and acetic acid. Yield = 62%. M.pt = 213° to 215° C.

| Analysis | Calculated | Found |
|---|---|---|
| C % | 58.47 | 58.48 |
| H % | 2.89 | 2.86 |
| Cl % | 20.31 | 20.38 |

NMR (DMSO $d_6$) δ (ppm) with reference to tetramethylsilane, 2 H at 3.85 (singlet), 1 H at 6.7 (singlet), 6 H from 7.4 to 8.4 (spread), 1 H from 1 to 4.5 (spread).

EXAMPLE 19

2-[2'-(2'',4''-Dichlorophenyl)-6'-chromonyl]propionic acid (a) Methyl 6-[2-(2',4'-Dichlorophenyl)chromonyl]acetate

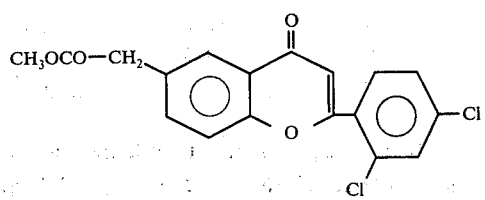

Empirical formula $C_{18}H_{12}Cl_2O_4$. Molecular weight = 363.

A solution of 16.3 g of 6-[2-(2',4'-dichlorophenyl)chromonyl]acetic acid in 200 ml of methanol and 10 ml of concentrated sulphuric acid is refluxed for six hours. The solution is cooled and the precipitate filtered. The precipitate is washed with 500 ml of 5% sodium bicarbonate and with water. Yield = 78%. M.pt = 153° C (ethanol).

(b) Ethyl 2-[2'-(2",4"-Dichlorophenyl-6-chromonyl]-2-methyl malonate

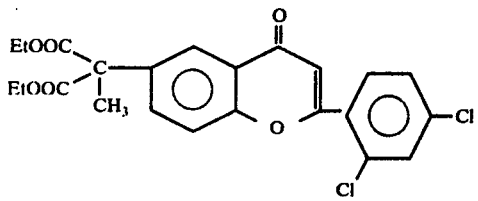

Empirical formula $C_{23}H_{20}Cl_2O_6$. Molecular weight = 463.317

This is prepared as described in Example 13(a). A white solid is obtained. Yield = 65%. M.pt = 110° C (di-isopropyl ether).

NMR (DMSO $d_6$) δ (ppm) with reference to tetramethylsilane, 6 H at 1.3 (triplet J = 7 cps), 3 H at 2 (singlet), 4 H at 4.3 (quartet J = 7 cps), 1 H at 6.7 (singlet), 6 H from 7.3 to 8.4 (spread).

(c) 2-[2'-(2",4"-Dichlorophenyl)-6'-chromonyl]propionic acid

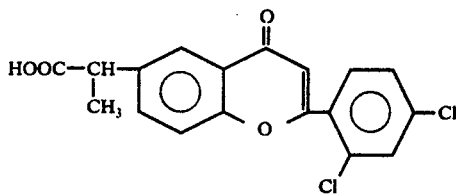

Empirical formula $C_{18}H_{12}Cl_2O_4$. M.pt = 363.19.

This is prepared as described in Example 13(b) from ethyl 2-[2'-(2",4"-dichlorophenyl)-6'-chromonyl]-2-methylmalonate. It is a white solid. Yield = 60%. M.pt. 194°-195° C (toluene)

| Analysis | Calculated | Found |
|---|---|---|
| 0 % | 59.52 | 59.61 |
| H % | 3.33 | 3.30 |
| Cl % | 19.52 | 19.48 |

NMR (DMSO $d_6$) δ (ppm) with reference to tetramethylsilane, 3 H at 1.5 (doublet J = 7 cps), 1 H at 3.95 (quartet J = 7 cps), 1 H spread from 3 to 4, 1 H at 6.65 (singlet), 6 H from 7 to 8.4 (spread).

EXAMPLE 20

6-[2-(p-Methylphenyl)chromonyl]acetic acid (Method B)

This is prepared as described in Example 18 making use of the following intermediates:

(a) 2'-Hydroxy-4"-methyl-5'-methoxymethyldibenzoylmethane

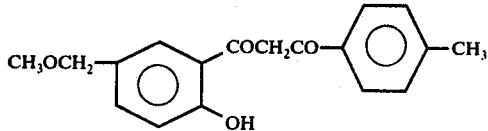

Empirical formula $C_{18}H_{18}O_4$. Molecular weight = 298.

The procedure is that described in Example 18(a) A yellow solid is obtained. Yield = 58%. M.pt = 87° to 88° C (di-isopropyl ether).

(b) 2-(4'-Methylphenyl)-6-bromomethylchromone

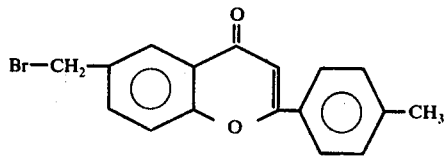

Empirical formula $C_{17}H_{13}Br\ O_2$. Molecular weight = 329.

The procedure is that described in Example 18(b) using the above dibenzoylmethane. A white solid is obtained. Yield = 60%. M.pt = 197° C (acetone + dimethylformamide).

(c) 2-(4'-Methylphenyl)-6-cyanomethylchromone

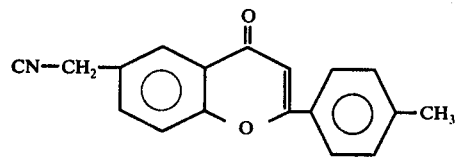

Empirical formula $C_{18}H_{13}N\ O_2$. Molecular weight = 275.

By proceeding as described in Example 18(c) using the above bromomethylchromone. A white solid is obtained. Yield = 62%. M.pt = 197° C (Water + ethanol + dimethylformamide).

NMR (DMSO $d_6$) δ(ppm) with reference to tetramethylsilane, 3 H at 2.4 (singlet), 2 H at 4.25 (singlet), 1 H at 7 (singlet), 7 H from 7.2 to 8.3 (spread).

(d) 6-[2-(p-Methylphenyl)chromonyl]acetic acid

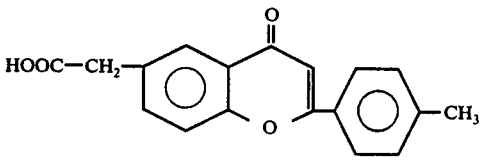

Empirical formula $C_{18}H_{14}O_4$. Molecular weight = 294.

After proceeding as described in Example 18(d) using the above cyanomethylchromone. A white solid is obtained. Yield = 94%. M.pt = 226° to 228° C.

| Analysis | Calculated | Found |
|---|---|---|
| C % | 73.45 | 73.22 |

| Analysis | Calculated | Found |
|---|---|---|
| H % | 4.79 | 4.70 |

NMR (DMSO d₆) δ(ppm) with reference to tetramethylsilane, 3 H at 2.4 (singlet), 2 H at 3.85 (singlet), 1 H at 7 (singlet), 7 H from 7.2 to 8.4 (spread), 1 H from 11.7 to 13.3 (broad spread).

EXAMPLE 21

2-[2'-(p-Methylphenyl)-6-chromonyl]propionic acid (a) Methyl 6-[2-(p-methylphenyl)chromonyl]acetate

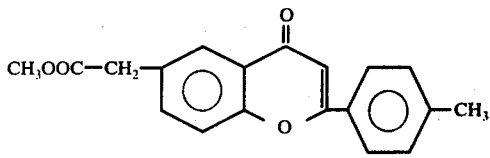

Empirical formula $C_{19}H_{16}O_4$. Molecular weight = 308.

This is prepared as described in Example 19(a). A white solid is obtained. Yield = 75%. M.pt = 145° C (methanol).

Ethyl 2-[6'-(2'-p-methylphenylchromonyl)]-2-methylmalonate

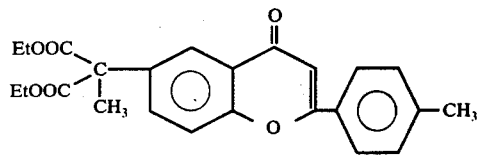

Empirical formula $C_{24}H_{24}O_6$. Molecular weight = 408.43.

After proceeding as described in Example 19(b) using the above acetate a light yellow solid is obtained. Yield = 58%. M.pt = 132° C.

NMR (deuterochloroform) δ(ppm) with reference to tetramethylsilane, 6 H at 1.3 (triplet J = 7 cps), 3 H at 2 (singlet), 3 H at 2.45 (singlet), 4 H at 4.3 (quartet 8 = 7 cps), 1 H at 6.8 (singlet), 7 H from 7.2 to 8.4 (spread).

2-[6'-(2'-p-methylphenyl)chromonyl]propionic acid

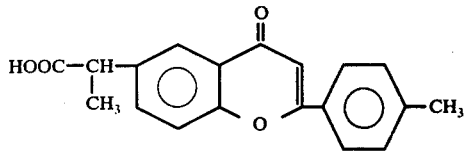

Empirical formula $C_{19}H_{16}O_4$. Molecular weight = 308.32.

After proceeding as described in Example 19(c) using the above malonate a white solid is obtained. Yield = 58%. M.pt = 196° to 198° C. Analysis Calculated Found C% 74.01 73.87 H% 5.23 5.26

NMR (DMSO d₆) δ (ppm) with reference to tetramethylsilane, 3 H at 1.55 (doublet J = 7 cps), 3 H at 2.40 (singlet), 1 H at 3.95 (quartet J = 7 cps), 1 H at 7 (singlet), 7 H from 7.2 to 8.4 (spread).

EXAMPLE 22

2-(6'-flavonyl)propionic acid (a) Ethyl 2-(6'-flavonyl)-2-methylmalonate

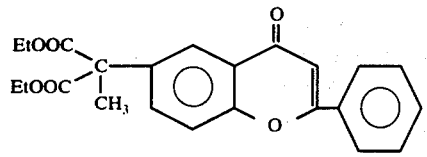

Empirical formula $C_{23}H_{22}O_6$. Molecular weight = 394.41.

After proceeding as described in Example 13 using methyl-6-flavonyl acetate, as starting material a white substance is obtained. Yield = 84%. M.pt = 99° to 100° C (di-isopropylether).

NMR (deuterochloroform) δ (ppm) relative to tetramethylsilane, 6 H at 0.9 (triplet J = 7 cps), 3 H at 1.6 (singlet), 4 H at 3.9 (quartet J = 7 cps), 1 H at 6.4 (singlet), 8 H from 7.2 to 8.1 (multiplet).

(b) 2-(6'-Flavonyl)propionic acid

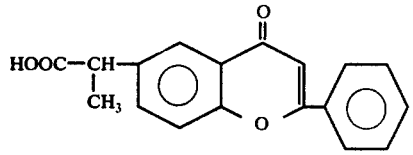

Empirical formula $C_{18}H_{14}O_4$. Molecular weight = 294.29

By proceeding as described in Example 13(b) starting with the above malonate a white solid is obtained. Yield = 80%. M.pt = 228° C (acetic acid).

| Analysis | Calculated | Found |
|---|---|---|
| C % | 73.46 | 73.36 |
| H % | 4.79 | 4.92 |

NMR (DMSO d₆) δ (ppm) with reference to tetramethylsilane, 3 H at 1.6 (doublet J = 7 cps), 2 H from 3.5 to 4.4 (quartet J = 7 cps on the spread), 1 H at 7.1 (singlet), 8 H from 7.4 to 8.4 (multiplet).

EXAMPLE 23

The acid oxalate of β-diethylaminoethyl 2-(6'-flavonyl) propionate

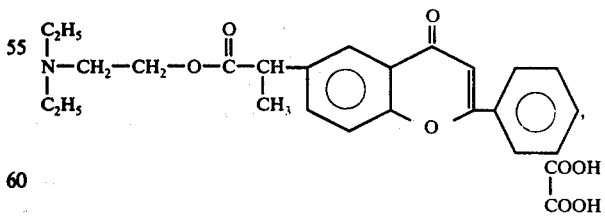

2.95 g (0.01 mole) of 6-flavonylpropionic acid is dissolved in 200 ml of alcohol and to it there is added drop by drop a solution of 0.56 g (0.01 mole) of potassium dissolved in alcohol. The alcohol is evaporated under reduced pressure and the residue dissolved in 50 ml of acetone. 1.35 g (0.01 mole) of β-chlorotriethylamine dissolved in 4 ml of acetone is then added. The mixture is refluxed for 3 hours and the acetone evaporated. The pasty residue is dissolved in chloroform and water. The organic phase is separated, washed with 5% sodium bicarbonate solution and water, then dried over sodium sulphate and the solvents evaporated. The oily residue is dissolved in 50 ml of ethanol and salified with oxalic acid. A white solid is obtained in a yield of 70%. M.pt = 150° to 153° C (ethanol)

| Analysis | Calculated | Found |
|---|---|---|
| C % | 63.69 | 63.68 |
| H % | 6.20 | 6.15 |
| N % | 2.97 | 3.03 |

EXAMPLE 24

Ethyl 2-(2'-phenyl-6'-chromonyl)propionate

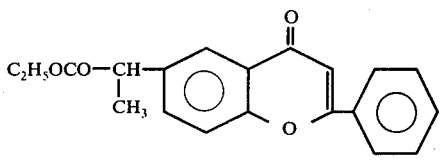

Empirical formula $C_{20}H_{18}O_4$. Molecular weight = 322.34.

A mixture of 20 g (0.68 mole) of 2-(6'-flavonyl) propionic acid, 28 ml of concentrated sulphuric acid and 1000 ml of anhydrous ethanol is refluxed for seven hours. The mixture is then poured into water and extracted a number of times with ether. The combined ethereal extracts are washed with 5% sodium bicarbonate solution dried and evaporated to dryness. The residual oil crystallises. Yield = 98%. M.pt = 74° to 76° C (di-isopropyl ether).

| Analysis | Calculated | Found |
|---|---|---|
| 0 % | 74.52 | 74.35 |
| H % | 5.63 | 5.75 |

EXAMPLE 25

Propyl 2-(2'-phenyl-6'-chromonyl)propionate

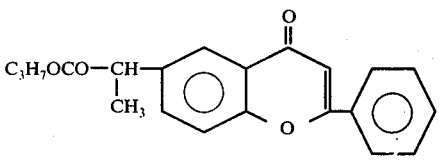

Empirical formula $C_{21}H_{20}O_4$. Molecular weight = 326.37.

This is prepared as described in Example 24 by esterification of 2-(6'-flavonyl)propionic acid with n-propanol. Yield = 55%. Melting point = 59° to 61° C (hexane). Analysis Calculated Found C% 74.98 75.26 H% 6.00 5.89

EXAMPLE 26

Isopropyl 2-(2'-phenyl-6'-chromonyl)propionate

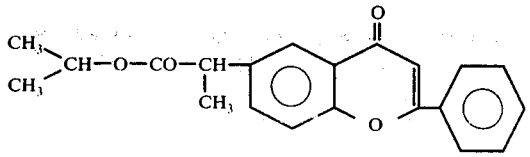

Empirical formula $C_{21}H_{20}O_4$. Molecular weight = 336.37.

This is prepared as described in Example 24 by esterification of 2-(6'-flavonyl)propionic acid with isopropanol. Yield = 80%. M.pt = 78° to 80° C (diisopropyl ether).

| Analysis | Calculated | Found |
|---|---|---|
| C % | 74.98 | 74.64 |
| H % | 6.00 | 5.97 |

EXAMPLE 27

Butyl 2-(2'-phenyl-6'-chromonyl)propionate

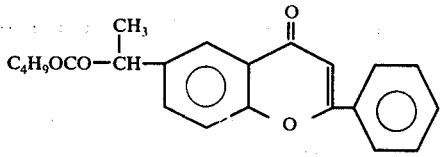

Empirical formula $C_{22}H_{22}O_4$. Molecular weight = 350.40.

By proceeding as described in Example 24, a white substance is obtained. Yield = 80%. M.pt = 44° to 46° C (hexane).

| Analysis | Calculated | Found |
|---|---|---|
| C % | 75.40 | 75.22 |
| H % | 6.33 | 6.35 |

EXAMPLE 28

β-Hydroxyethyl 2-(2'-phenyl-6'-chromonyl)propionate monohydrate

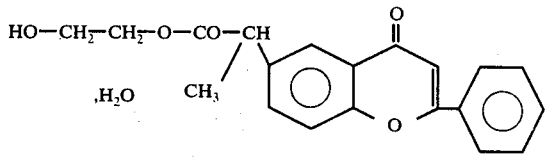

Empirical formula $C_{20}H_{20}O_6$. Molecular weight = 356.36.

A mixture of 11.8 g (0.04 mole) of 2-(6'-flavonyl) propionic acid, 100 ml of benzene, 100 ml of ethylene glycol, and 1.35 g of p-toluene sulphonic acid is refluxed for four hours in a flask fitted with a Dean and Stark apparatus. The reaction mixture is then poured into water. An oil separates, is decanted and crystallises yielding a white substance. Yield = 90%. M.pt = 79°–83° C (10 : 6 mixture of hexane and ethyl acetate).

| Analysis | Calculated | Found |
|---|---|---|
| C % | 67.40 | 67.22 |
| H % | 5.66 | 5.52 |

EXAMPLE 29

Methyl 2-[2'-(α-thienyl)-6'-chromonyl]propionate

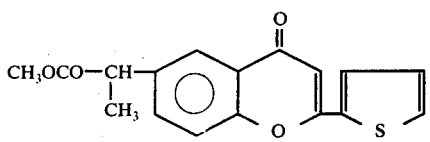

Empirical formula $C_{17}H_{14}SO_4$. Molecular weight = 314.34.

This is prepared as described in Example 24 by esterification, in the presence of sulphuric acid, of the acid of Example 13 with methanol. Yield = 80%. M.pt = 96° to 98° C (ethyl acetate).

| Analysis | Calculated | Found |
|---|---|---|
| C % | 64.96 | 65.24 |
| H % | 4.49 | 4.27 |
| S % | 10.20 | 10.28 |

EXAMPLE 30

Methyl 2-[2'-(β-thienyl)-6'-chromonyl]propionate

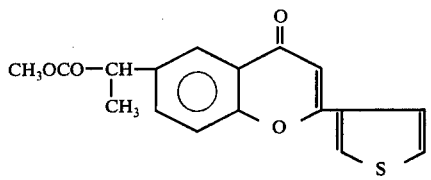

Empirical formula $C_{17}H_{14}SO_4$. Molecular weight = 314.34.

This is prepared as described in Example 24 by the esterification, in the presence of sulphuric acid, of the acid of Example 15 with methanol. Yield = 85%. M.pt = 95° to 98° C (di-isopropyl ether)

| Analysis | Calculated | Found |
|---|---|---|
| C % | 64.95 | 65.10 |
| H % | 4.49 | 4.47 |
| S % | 10.20 | 10.20 |

EXAMPLE 31

Propyl 2-(2'-α-thienyl-6'-chromonyl)propionate

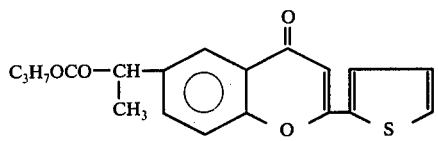

Empirical formula $C_{19}H_{18}O_4S$. Molecular weight = 342.33.

This is prepared as described in Example 25 from the acid of Example 13. A white solid is obtained. Yield = 90%. M.pt = 48° to 52° C.

| Analysis | Calculated | Found |
|---|---|---|
| C % | 66.66 | 66.47 |
| H % | 5.29 | 5.27 |
| S % | 9.36 | 9.40 |

EXAMPLE 32

The acid oxalate of β-morpholinoethyl-2-[2'-(α-thienyl)-6'-chromonyl]propionate

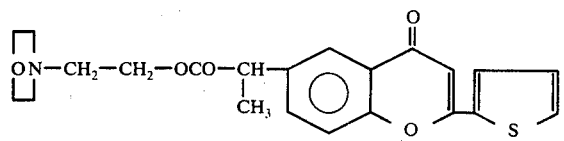

$C_{24}H_{25}NO_9S$. Molecular weight = 503.5.

A mixture of 12 g (0.04 mole) of 2-[2'-(α-thienyl)-6'-chromonyl]propionic acid, 2.55 g (0.04 mole) of potassium, and 500 ml of methanol is refluxed for 30 minutes. The solvent is evaporated to dryness under reduced pressure and the powdery residue is dissolved in 50 ml of methyl isobutyl ketone and 10.5 g of freshly distilled chloroethylmorpholine. The mixture is refluxed for 8 hours and the solids filtered.

The methyl isobutyl ketone is evaporated from the organic phase under reduced pressure and the oily residue immediately salified with oxalic acid dissolved in acetone. The salt obtained is purified by recrystallisation from a 6 : 1 mixture of acetone and water. Yield: = 70%. M.pt = 167° to 170° C (ethanol).

| Analysis | Calculated | Found |
|---|---|---|
| C % | 57.25 | 57.27 |
| H % | 5.00 | 4.97 |
| N % | 2.78 | 2.71 |
| S % | 6.36 | 6.01 |

EXAMPLE 33

6-[2-(2'-phenoxyphenyl)-chromonyl]acetic acid (Method B)

This is prepared as described in Example 18 through the following intermediates:

(a)
2'-Hydroxy-2''-phenoxy-5'-methoxymethyldibenzoylmethane

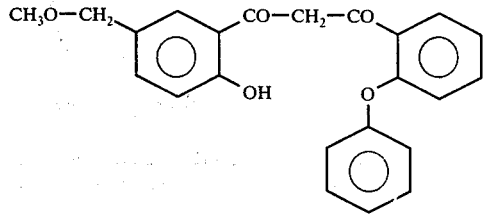

Empirical formula $C_{23}H_{20}O_5$. Molecular weight = 376.39.

After proceeding as described in Example 18(a), a yellow solid is obtained. Yield = 75%. M.pt = 94° C (di-isopropyl ether).

(b) 2-(2'-Phenoxyphenyl)-6-bromomethylchromone

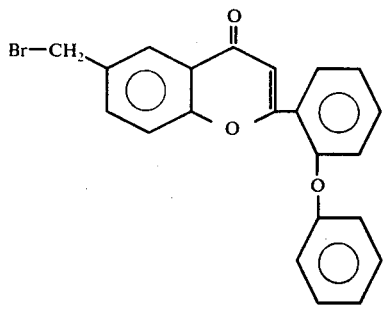

Empirical formula $C_{22}H_{15}BrO_3$. Molecular weight = 407.25

After proceeding as described in Example 18(b), a white solid is obtained. Yield = 71%. M.pt = 145° C (acetone).

(c) 2-(2'-Phenoxyphenyl)-6-cyanomethylchromone

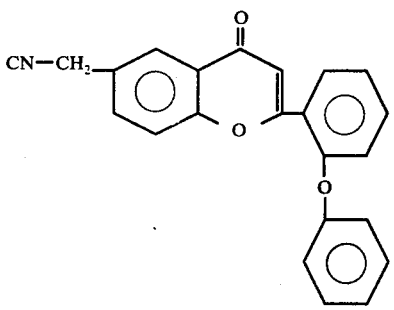

Empirical formula $C_{23}H_{15}NO_3$. Molecular weight = 353.35

After proceeding as described in Example 18(c), a white solid is obtained. Yield = 38%. M.pt = 138° C (ethanol).

(d) 6-[2-(2'-Phenoxyphenyl)chromonyl]acetic acid

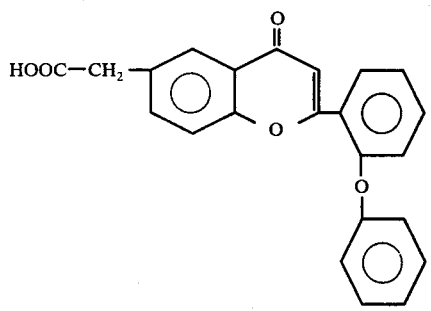

Empirical formula $C_{23}H_{16}O_5$. Molecular weight = 372.36.

After proceeding as described in Example 18(d), a white solid is obtained. Yield = 63%. M.pt = 17° C (ethanol).

NMR (deuterochloroform) δ (ppm) with reference to tetramethylsilane, 2 H at 3.8 (singlet), 1 H from 5.2 to 5.5 (broad spread), 13 H from 6.9 to 8.3 (spread).

EXAMPLE 34

2-[2'-(2''-Phenoxyphenyl)-6'-chromonyl]propionic acid (a) Methyl 6-[2-(2'-phenoxyphenyl)chromonyl]acetate

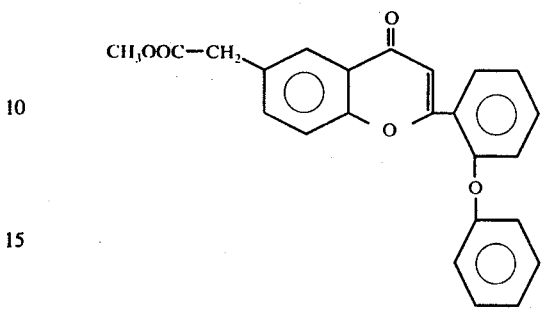

Empirical formula $C_{24}H_{18}O_5$. Molecular weight = 386.38.

This is prepared as described in Example 19(a). A white solid is obtained. Yield = 65%. M.pt = 125° C (methanol).

(b) Ethyl 2-[2'-(2''-phenoxyphenyl)-6'-chromonyl]-2-methyl malonate

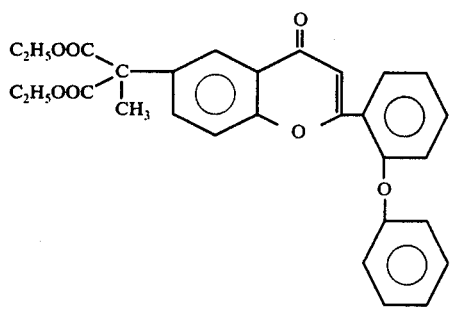

Empirical formula $C_{29}H_{26}O_7$. Molecular weight = 486.50

This is prepared as described in Example 19(b). A brown oil which cannot be crystallised is obtained. Yield = 58%.

NMR (deuterochloroform) δ (ppm) with reference to tetramethylsilane, 6 H at 1.3 (triplet J = 7 cps), 3 H at 1.9 (singlet), 4 H at 4.2 (quartet J = 7 cps), 13 H from 6.8 to 8.1 (spread), (c) 2-[2'-(2''-Phenoxyphenyl)-6'-chromonyl]propionic acid

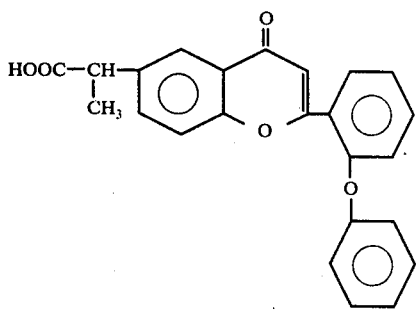

Empirical formula $C_{24}H_{18}O_5$. Molecular weight = 386.38.

After proceeding as described in Example 19(c), a white solid is obtained. Yield = 50% M.pt = 175° to 178° C (isopropanol) NMR (DMSO d$_6$) δ (ppm) with reference to tetramethylsilane, 3 H at 1.55 (doublet J = 7 cps), 2 H from 3.8 to 4.2 (quadruplet J = 7 cps spread), 13 H from 6.9 to 8.2 (spread).

| Analysis | Calculated | Found |
|---|---|---|
| C % | 74.60 | 74.35 |
| H % | 4.69 | 4.51 |

EXAMPLE 35

2-[2'-(3''-Trifluoromethylphenyl)-6'-chromonyl]propionic acid (a) Methyl [2-(3'-trifluoromethylphenyl)-6-chromonyl]acetate Empirical formula C$_{19}$H$_{13}$F$_3$O$_4$. Molecular weight = 361.

This is prepared as described in Example 19(a) by esterification, in the presence of sulphuric acid, of 6-(2-m-trifluoromethylphenylchromonyl)acetic acid. Yield = 83%. M.pt = 140° C (methanol).

NMR (DMSO d$_6$) δ (ppm) relative to tetramethylsilane, 3 H at 3.30 (singlet), 2 H at 3.40 (singlet), 1 H at 6.65 (singlet), 7 H from 7.20 to 8.00 (multiplet).

(b) Ethyl 2-[2'-(3''-trifluoromethylphenyl)-6'-chromonyl]-2-methylmalonate

Empirical formula C$_{24}$H$_{21}$F$_3$O$_6$. Molecular weight = 462.41.

This is prepared as described in Example 19(b). A white solid is obtained. Yield = 64%. M.pt = 82° to 83° C (di-isopropyl ether).

NMR (carbon tetrachloride) δ (ppm) with reference to tetramethylsilane, 6 H at 1.3 (triplet J = 7 cps), 3 H at 1.9 (singlet), 4 H at 4.2 (quartet J = 7 cps), 1 H at 6.8 (singlet), 7 H from 7.3 to 8.3 (multiplet).

(c) 2-[2'-(3''-Trifluoromethylphenyl)-6'-chromonyl]propionic acid

Empirical formula C$_{19}$H$_{13}$O$_4$F$_3$. Molecular weight = 362.19

After proceeding as described in Example 19(c), a white solid is obtained. Yield = 60%. M.pt 171° to 173° C (toluene).

| Analysis | Calculated | Found |
|---|---|---|
| C % | 63.00 | 63.16 |
| H % | 3.62 | 3.56 |
| F % | 15.74 | 15.82 |

NMR (DMSO d$_6$) δ (ppm) with reference to tetramethylsilane, 3 H at 1.6 (doublet J = 7 cps), 2 H from 3.4 to 4.4 (quartet J = 7 cps), 1 H at 7.3 (singlet), 7 H from 7.8 to 8.6 (multiplet).

We claim:

1. A carboxychromonyl compound having the formula in which X is selected from the group consisting of phenyl, halophenyl, polyhalophenyl, lower alkylphenyl, and trihalomethylphenyl; and R is selected from the group consisting of hydrogen, lower alkyl, lower omega-hydroxyalkyl, morpholinoethyl and lower dialkylaminoalkyl, together with (a) salts of said compound with pharmaceutically acceptable acids when R is morpholinoethyl and lower dialkylaminoalkyl and (b) salts of said compound with pharmaceutically acceptable mineral and organic bases when R is hydrogen.

2. A compound in accordance with claim 1 wherein R is hydrogen, lower alkyl or lower omega-hydroxyalkyl.

3. A carboxychromonyl compound having the formula:

in which X is phenyl and R is hydrogen, lower alkyl or lower omega-hydroxyalkyl, lower dialkylaminoalkyl, together with (a) salts of said compound with pharmaceutically acceptable acids when R is a lower dialkylaminoalkyl and (b) salts of said compound with pharmaceutically acceptable mineral and organic bases when R is hydrogen.

4. A carboxychromonyl compound having the formula:

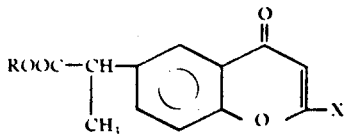

in which X is phenyl and R is hydrogen, lower alkyl or lower omega-hydroxyalkyl; or a pharmaceutically acceptable salt thereof.

5. A compound in accordance with claim 4 selected from the group consisting of 2-(6-flavonyl)-propionic acid, and propyl-2-(2'-phenyl-6'-chromonyl) propionate.

6. The compound of claim 4 which is 2-(6-flavonyl)-propionic acid.

7. The compound which is 2-(6-flavonyl)-propionic acid or a pharmaceutically acceptable salt or ester thereof.

8. An analgesic and anti-inflammatory pharmaceutical composition which comprises (a) the carboxychromonyl compound claimed in claim 4 in an amount sufficient to provide analgesic and anti-inflammatory activity together with (b) a pharmaceutically acceptable diluent therefor.

9. The composition of claim 8 in the form of tablets.

10. An analgesic and anti-inflammatory pharmaceutical composition which comprises (a) 2-(6-flavonyl) propionic acid in an amount sufficient to provide analgesic and anti-inflammatory activity, together with (b) a pharmaceutically acceptable diluent therefor.

* * * * *